(12) United States Patent
Sugiyama et al.

(10) Patent No.: US 6,332,965 B1
(45) Date of Patent: Dec. 25, 2001

(54) COMPOSITE GAS SENSOR

(75) Inventors: Tomio Sugiyama, Nagoya; Naoto Miwa, Tsushima; Masahiro Shibata, deceased, late of Nagoya, by Midori Shibata, Natsumi Shibata, Raina Shibata, legal representatives; Hiromi Sano, Nagoya; Akio Tanaka, Oobu, all of (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 09/100,230

(22) Filed: Jun. 19, 1998

(30) Foreign Application Priority Data

Jun. 20, 1997 (JP) .................................................. 9-180446
Nov. 26, 1997 (JP) .................................................. 9-342217

(51) Int. Cl.⁷ .................................................. G01N 27/26
(52) U.S. Cl. ........................ 204/425; 204/426; 205/781
(58) Field of Search .................................. 204/425, 426, 204/427; 205/781, 784.5, 785

(56) References Cited

U.S. PATENT DOCUMENTS

| 4,472,262 | * | 9/1984 | Kondo et al. ........................ 204/425 |
| 4,824,549 | | 4/1989 | Hamada et al. . |
| 5,672,811 | | 9/1997 | Kato et al. . |
| 5,772,965 | * | 6/1998 | Kato et al. .......................... 422/98 |
| 5,877,406 | * | 3/1999 | Kato .................................. 73/23.31 |
| 6,036,841 | * | 3/2000 | Kato et al. ........................... 205/781 |

FOREIGN PATENT DOCUMENTS

| 678 740 A1 | * | 10/1995 | (EP) . |
| 8-271476 | | 10/1996 | (JP) . |
| 30146 | * | 11/1995 | (WO) . |

OTHER PUBLICATIONS

Kato et al "Thick Film ZrO2 NOx Sensor", paper 960334, pp. 137–142, 1996 (month unavailable).*

* cited by examiner

Primary Examiner—Robert J. Warden, Sr.
Assistant Examiner—Kaj K. Olsen
(74) Attorney, Agent, or Firm—Pillsbury Winthrop LLP

(57) ABSTRACT

A composite gas sensor comprises a pump cell, a NOx sensor cell and an oxygen sensor cell. The NOx sensor cell is connected to a first ammeter and a constant power source to measure the NOx concentration of a sample gas. The pump cell is connected to a second ammeter and a variable power source to measure an air-fuel ratio of the sample gas. The oxygen sensor cell is connected to a voltmeter. A controller adjusts the variable power source to produce a constant value from the voltmeter.

6 Claims, 10 Drawing Sheets

COMPOSITE GAS SENSOR

BACKGROUND OF THE INVENTION

The present invention relates to a gas concentration measuring method and a related composite gas sensor preferably used in an exhaust gas purification system employed in an internal combustion engine of an automotive vehicle.

Exhaust gases emitted from the internal combustion engines are main causes of the present-days serious air pollution. To suppress any harmful substances involved in the exhaust gas, the related laws and regulations have been becoming severe year by year.

In view of the foregoing, the air-fuel ratio of the gas mixture supplied to a combustion chamber of the internal combustion engine must be precisely controlled. Similarly, the ignition timing of the internal combustion engine must be carefully controlled. Furthermore, many of the internal combustion engines are equipped with catalytic converters to purify the exhaust gas.

According to the OBD-II regulation in the United States, each purification system is required to have the capability of judging whether or not the catalytic converter operates properly. To this end, an advanced exhaust gas purification system proposes to directly measure the harmful substances, i.e., NOx concentration, as well as precisely controlling the engine combustion.

In general, the catalytic converter is disposed in an exhaust gas passage of an internal combustion engine. When the catalytic converter deteriorates, an increased amount of NOx gas flows across the catalytic converter. In other words, the deterioration of the catalytic converter can be known by the increase amount of the NOx gas not trapped by the catalytic converter. Accordingly, an appropriate NOx sensor is provided downstream of the catalytic converter to detect the change of NOx concentration.

SUMMARY OF THE INVENTION

An object of the present invention is to provide a gas concentration measuring method for simultaneously measuring both the NOx concentration and the air-fuel ratio of a sample gas.

Another object of the present invention is to provide a gas concentration measuring method for simultaneously measuring all of the NOx concentration, the air-fuel ratio and the oxygen concentration of the sample gas.

Another object of the present invention is to provide a gas concentration measuring method for measuring a sample gas temperature as well as the NOx gas concentration and the air-fuel ratio of the sample gas.

Another object of the present invention is to provide a composite gas sensor preferably used in these measuring methods.

In order to accomplish this and other related objects, various aspects of the present invention provides gas concentration measuring methods and related composite gas sensors.

According to a first aspect of the present invention, the composite gas sensor comprises:

oxygen ion conductive solid electrolytic substrates defining at least part of a reference gas chamber and a sample gas chamber;

a sample gas introducing passage introducing a sample gas to the sample gas chamber;

a pump cell having a pair of pumping electrodes for adjusting an oxygen gas amount introduced or exhausted into or from the sample gas chamber, one of the pumping electrodes facing the sample gas chamber and the other of the pumping electrodes facing an outside of the composite gas sensor;

a first sensor cell having a pair of NOx sensing electrodes for detecting a NOx concentration in the sample gas chamber, one of the NOx sensing electrodes facing the sample gas chamber and the other of the NOx sensing electrodes facing the reference gas chamber;

a second sensor cell having a pair of oxygen sensing electrodes for detecting an oxygen concentration in the sample gas chamber, one of the oxygen sensing electrodes facing the sample gas chamber and the other of the oxygen sensing electrodes facing the reference gas chamber;

a first detecting circuit including a first ammeter and an electric power source connected to the first sensor cell for measuring a sensing current of the first sensor cell;

a pump circuit including a second ammeter and a variable electric power source connected to the pump cell for measuring a current of the pump cell; and a second detecting circuit including a first voltmeter connected to the second sensor cell for measuring a sensing voltage of the second sensor cell.

Using the above-described composite gas sensor, the gas concentration measuring method in accordance with the first aspect of the present invention comprises the steps of:

controlling the variable electric power source of the pump circuit to produce a constant value from the first voltmeter;

measuring the NOx concentration of the sample gas based on a measurement by the first ammeter; and measuring an air-fuel ratio of the sample gas based on a measurement by the second ammeter.

Furthermore, the gas concentration measuring method in accordance with the first aspect of the present invention comprises the step of measuring an oxygen concentration of the sample gas based on a measurement by a second voltmeter connected between the other pumping electrode facing the outside of the composite gas sensor and the other oxygen sensing electrode facing the reference gas chamber.

According to the first aspect of the present invention, it is preferably that the sample gas chamber includes a first chamber and a second chamber communicating with each other via a diffusive passage. The sample gas introducing passage is directly connected to the first chamber. The one of the pumping electrodes faces the first chamber. The one of the NOx sensing electrodes faces the second chamber. And, the one of the oxygen sensing electrodes faces the second chamber.

Furthermore, the composite gas sensor may comprise a third detecting circuit including a second voltmeter connected between an external electrode facing the outside of the composite gas sensor and the other oxygen sensing electrode facing the reference gas chamber, and an oxygen concentration detector associated with the third detecting circuit for measuring an oxygen concentration of the sample gas based on a measurement by the second voltmeter.

It is further preferable that the sample gas chamber and the reference gas chamber are provided at a same surface level.

It is further preferable that the other NOx sensing electrode and the other oxygen sensing electrode are a common electrode facing the reference gas chamber.

It is further preferable that the sample gas introducing passage is a pinhole. Alternatively, the sample gas introduction passage may be formed by a porous layer having a porosity larger than that of the solid electrolytic substrates.

According to a second aspect of the present invention, the composite gas sensor comprising:

oxygen ion conductive solid electrolytic substrates defining at least part of a reference gas chamber and a sample gas chamber;

a sample gas introducing passage introducing a sample gas to the sample gas chamber;

a pump cell having a pair of pumping electrodes for adjusting an oxygen gas amount introduced or exhausted into or from the sample gas chamber, one of the pumping electrodes facing the sample gas chamber and the other of the pumping electrodes facing an outside of the composite gas sensor;

a first sensor cell having a pair of NOx sensing electrodes for detecting a NOx concentration in the sample gas chamber, one of the NOx sensing electrodes facing the sample gas chamber and the other of the NOx sensing electrodes facing the reference gas chamber;

a second sensor cell having a pair of oxygen sensing electrodes for detecting an oxygen concentration in the sample gas chamber, one of the oxygen sensing electrodes facing the sample gas chamber and the other of the oxygen sensing electrodes facing the reference gas chamber;

a first detecting circuit including a first ammeter and an electric power source connected to the first sensor cell for measuring a sensing current of the first sensor cell;

a pump circuit including a second ammeter and a variable electric power source connected to the pump cell for measuring a current of the pump cell;

a second detecting circuit including a first voltmeter connected to the second sensor cell for measuring a sensing voltage of the second sensor cell; and an impedance detector associated with the pump circuit for measuring an impedance of the pump cell.

Using the above-described composite gas sensor, the gas concentration measuring method in accordance with the second aspect of the present invention comprises the steps of:

controlling the variable electric power source of the pump circuit to produce a constant value from the first voltmeter;

measuring the NOx concentration of the sample gas based on a measurement by the first ammeter;

measuring an air-fuel ratio of the sample gas based on a measurement by the second ammeter; and measuring a sample gas temperature based on a measurement by the impedance detector.

Furthermore, according to a third aspect of the present invention, the composite gas sensor comprising:

oxygen ion conductive solid electrolytic substrates defining at least part of a reference gas chamber and a sample gas chamber;

a sample gas introducing passage introducing a sample gas to the sample gas chamber;

a pump cell having a pair of pumping electrodes for adjusting an oxygen gas amount introduced or exhausted into or from the sample gas chamber, one of the pumping electrodes facing the sample gas chamber and the other of the pumping electrodes facing an outside of the composite gas sensor;

a first sensor cell having a pair of NOx sensing electrodes for detecting a NOx concentration in the sample gas chamber, one of the NOx sensing electrodes facing the sample gas chamber and the other of the NOx sensing electrodes facing the reference gas chamber;

a second sensor cell having a pair of oxygen sensing electrodes for detecting an oxygen concentration in the sample gas chamber, one of the oxygen sensing electrodes facing the sample gas chamber and the other of the oxygen sensing electrodes facing the reference gas chamber;

a temperature detecting cell having a porous substrate provided on the pump cell and a resistor provided on an outer surface of the porous substrate;

a first detecting circuit including a first ammeter and an electric power source connected to the first sensor cell for measuring a sensing current of the first sensor cell;

a pump circuit including a second ammeter and a variable electric power source connected to the pump cell for measuring a current of the pump cell; and a second detecting circuit including a first voltmeter connected to the second sensor cell for measuring a sensing voltage of the second sensor cell.

Using the above-described composite gas sensor, the gas concentration measuring method in accordance with the third aspect of the present invention comprises the steps of:

controlling the variable electric power source of the pump circuit to produce a constant value from the first voltmeter;

measuring the NOx concentration of the sample gas based on a measurement by the first ammeter;

measuring an air-fuel ratio of the sample gas based on a measurement by the second ammeter; and measuring a sample gas temperature based on a measured resistance value of the resistor in the temperature detecting cell.

BRIEF DESCRIPTION OF THE DRAWINGS

The above and other objects, features and advantages of the present invention will become more apparent from the following detailed description which is to be read in conjunction with the accompanying drawings, in which.

DESCRIPTION OF THE PREFERRED EMBODIMENTS

Figure 1:
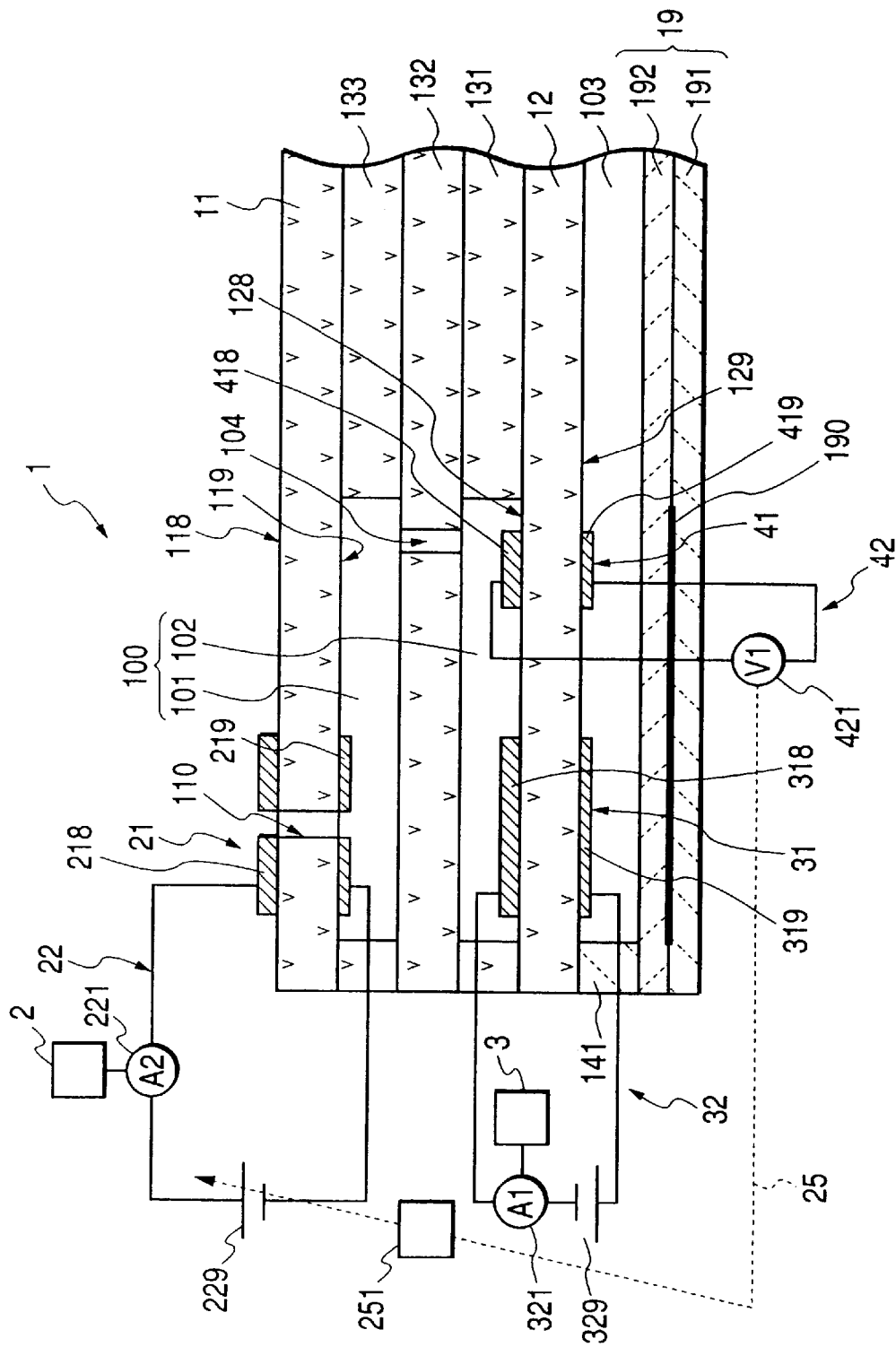
FIG. 1 is a cross-sectional view showing an arrangement of a composite gas sensor in accordance with a first embodiment of the present invention.

Preferred embodiments of the present invention will be explained hereinafter with reference to attached drawings. Identical parts are denoted by the same reference numerals throughout the views. In the following explanation, an up-and-down direction is defined based on the layout shown in each figure. Needless to say, an actual up-and-down direction of a gas concentration sensor may be changed when it is installed on an internal combustion engine.

First Embodiment

Figure 2:
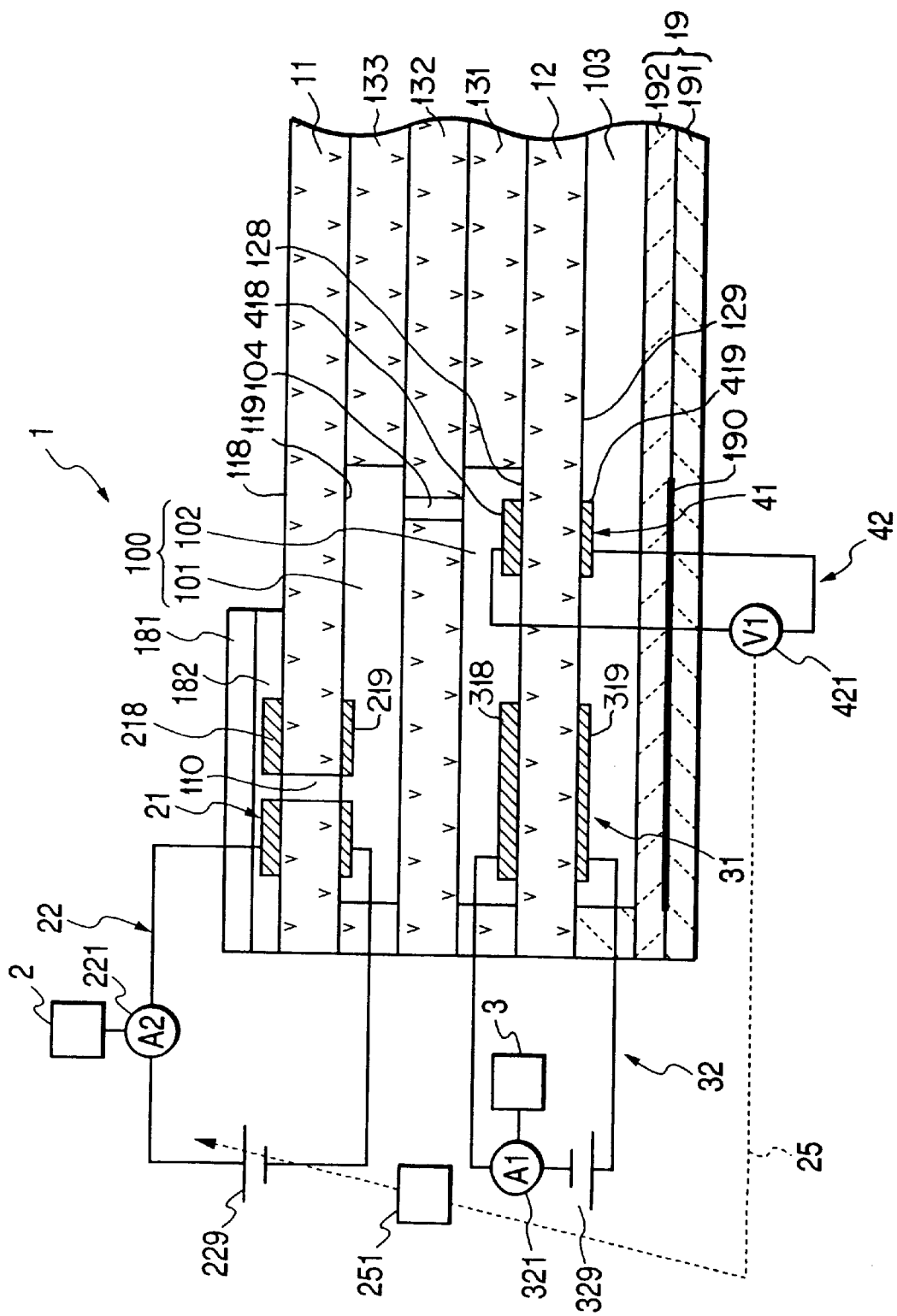
FIG. 2 is a cross-sectional view showing a modified arrangement of the composite gas sensor in accordance with the first embodiment of the present invention.
Figure 3:
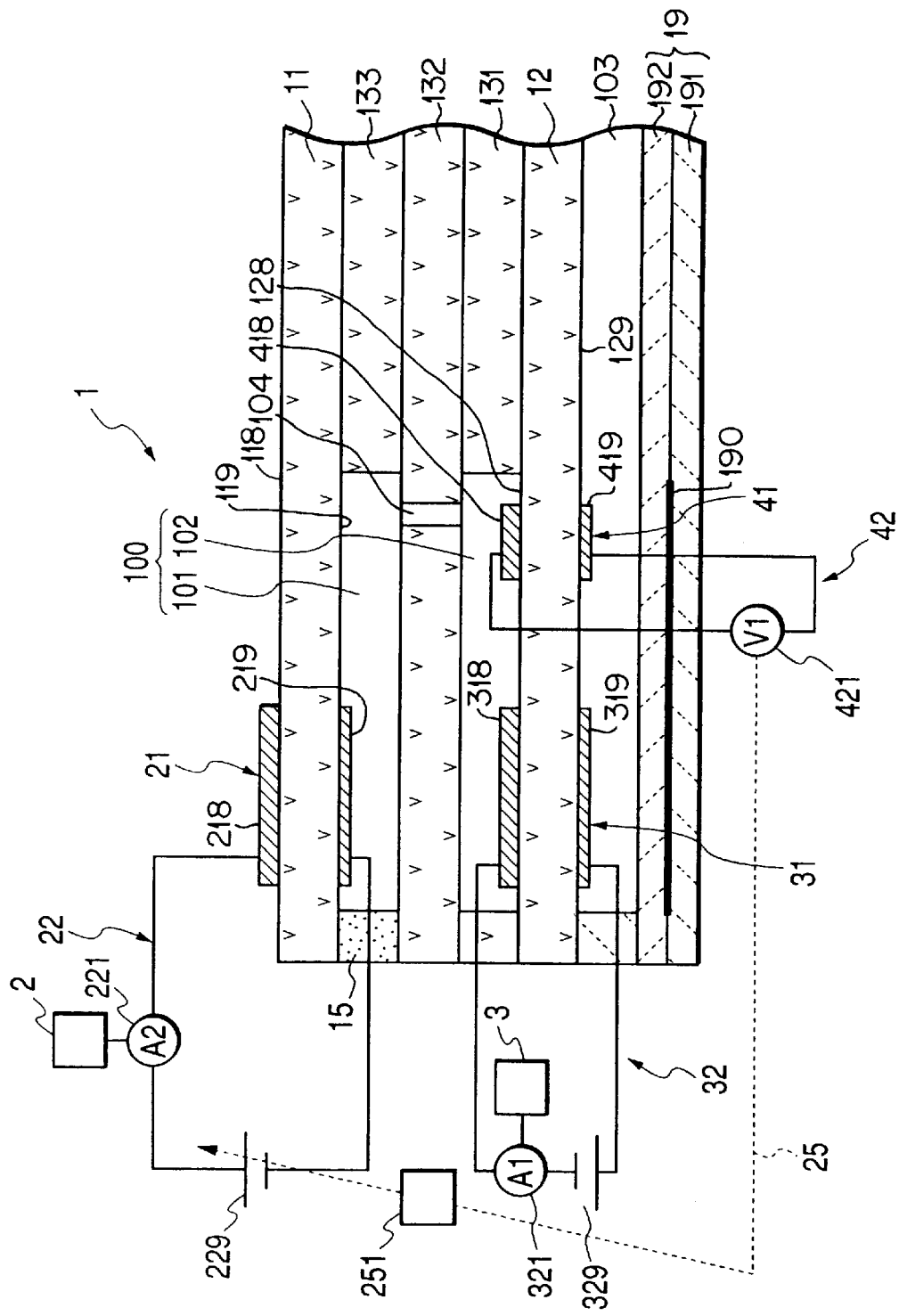
FIG. 3 is a cross-sectional view showing another modified arrangement of the composite gas sensor in accordance with the first embodiment of the present invention.

FIGS. 1 through 3 are cross-sectional views showing preferable arrangements of a composite gas sensor in accordance with a first embodiment of the present invention.

As shown in FIG. 1, a composite gas sensor 1 of the first embodiment comprises a sample gas chamber 100 and a reference gas chamber 103. At least part of the sample gas chamber 100 and the reference gas chamber 103 is defined by first and second solid electrolytic substrates 11 and 12, respectively. The first and second solid electrolytic substrates 11 and 12 are made of an oxygen ion conductive material. A pinhole 110 extends across the first solid electrolytic substrate 11 from an upper surface to a lower surface thereof. A lower end of the pinhole 110 communicates with the sample gas chamber 100. A sample gas is introduced from the outside to the sample gas chamber 100 via the pinhole 110.

A pump cell 21 comprises a pair of pumping electrodes 218 and 219 formed on an upper surface 118 and a lower surface 119 of the first solid electrolytic substrate 11, respectively. The above-described pinhole 110 has an upper end opened at a center of the upper pumping electrode 218 and a lower end opened at a center of the lower pumping electrode 219. The upper pumping electrode 218 is exposed to the outside. The lower surface 119 of the first solid electrolytic substrate 11 defines a ceiling of the sample gas chamber 100. The lower pumping electrode 219 extends along the ceiling of the sample gas chamber 100. The pump cell 21 adjusts an amount of the oxygen gas introduced or exhausted into or from the sample gas chamber 100.

A first sensor cell 31 comprises a pair of sensing electrodes 318 and 319 formed on an upper surface 128 and a lower surface 129 of the second solid electrolytic substrate 12, respectively. The upper surface 128 of the second solid electrolytic substrate 12 defines a bottom of the sample gas chamber 100. The upper sensing electrode 318 extends along the bottom of the sample gas chamber 100. The lower surface 129 of the second solid electrolytic substrate 12 defines a ceiling of the reference gas chamber 103. The lower sensing electrode 319 extends along the ceiling of the reference gas chamber 103. The first sensor cell 31 detects the concentration of the NOx gas residing in the sample gas chamber 100.

A second sensor cell 41 comprising a pair of sensing electrodes 418 and 419 formed on the upper surface 128 and the lower surface 129 of the second solid electrolytic substrate 12, respectively. The upper sensing electrode 418 extends along the bottom of the sample gas chamber 100. The lower sensing electrode 419 extends along the ceiling of the reference gas chamber 103. The second sensor cell 41 detects the concentration of the oxygen gas residing in the sample gas chamber 100.

The first sensor cell 31 is serially connected with a first ammeter 321 and an electric power source 329, thereby constituting a first detecting circuit 32. The pump cell 21 is serially connected with a second ammeter 221 and a variable electric power source 229, thereby constituting a pump circuit 22. The second sensor cell 41 is serially connected with a first voltmeter 421, thereby constituting a second detecting circuit 42.

A controller 251 feedback controls the variable electric power source 229 in response to an output value of the first voltmeter 421. In other words, the controller 251 and the first voltmeter 421 cooperatively operate as a feedback circuit 25 for controlling the variable electric power source 229. With this feedback control, the output value of the first voltmeter 421 is maintained at a constant value.

A NOx concentration detector 3 is connected with the first ammeter 321. The NOx concentration detector 3 measures the concentration of the NOx gas residing in the sample gas chamber 100 based on an output value of the first ammeter 321. The output of the first ammeter 321 is proportional to a sum of a variable NOx concentration and a constant oxygen concentration in the sample gas chamber 100. Thus, the NOx concentration can be measured from the output value of the first ammeter 321.

An air-fuel ratio detector 2 is connected with the second ammeter 221. The air-fuel ratio detector 2 measures the air-fuel ratio of the sample gas residing in the sample gas chamber 100 based on an output value of the second ammeter 221. The output value of the second ammeter 221 is proportional to an oxygen amount, i.e., the air-fuel ratio, of the sample gas.

The sample gas chamber 100 consists of a first chamber 101 and a second chamber 102 partitioned by an intervening substrate 132. A diffusive passage 104 extends across the intervening substrate 132 from the first chamber 101 to the second chamber 102. Thus, the first chamber 101 communicates with the second chamber 102 via the diffusive passage 104.

The above-described pinhole 110 and the lower pumping electrode 219 of the pump cell 21 face the first chamber 101. The upper sensing electrode 318 of the first sensor cell 31 and the upper sensing electrode 418 of the second sensor cell 41 face the second chamber 102.

The first solid electrolytic substrate 11 defines a ceiling of the first chamber 101. The substrate 132 defines a bottom of the first chamber 101. A substrate 133, interposed between the first solid electrolytic substrate 11 and the substrate 132, has an aperture defining the side walls of the first chamber 101.

The substrate 132 defines a ceiling of the second chamber 102. The second solid electrolytic substrate 12 defines a bottom of the second chamber 102. A substrate 131, interposed between the substrate 132 and the second solid electrolytic substrate 12, has an aperture defining the side walls of the second chamber 102.

A bottom of the reference gas chamber 103 is defined by an upper surface of a heater 19 integrally provided at the lower end of the composite gas sensor 1. A substrate 141, interposed between the second solid electrolytic substrate 12 and the heater 19, has an aperture (slit) defining the side walls of the reference gas chamber 103.

The heater 19 comprises a heater substrate 191. A heater element 190 is mounted on this heater substrate 191 as a heat generating source. The heater element 190 is covered by a coating plate 192.

As described above, the controller 251 feedback controls the variable electric power source 229 to produce a constant output from the first voltmeter 421.

With this arrangement, the composite gas sensor 1 measures the NOx concentration of the sample gas based on the output value of the first ammeter 321 and measures the air-fuel ratio of the sample gas based on the output value of the second ammeter 221.

As shown in FIG. 1, the composite gas sensor 1 has a multilayered body comprising the first and second solid electrolytic substrates 11~12, the substrates 131~133, 141 and the heater 19. The substrates 131, 132 and 133 are made of the same material as that of the first and second solid electrolytic substrates 11 and 12. The substrate 141 is made of the same material as that of the heater substrate 191 and the coating plate 192.

The pumping electrodes 218 and 219 of the pump cell 21 are connected to the pump circuit 22 via leads (not shown) and terminals (not shown) formed on the surfaces of the first solid electrolytic substrate 11.

The lower pumping electrode 219 is made of Pt with an Au additive and inactive against NOx. The upper pumping electrode 218 is made of Pt.

The sensing electrodes 318 and 319 of the first sensor cell 31 are connected to the first detecting circuit 32 via leads (not shown) and terminals (not shown) formed on the surfaces of the second solid electrolytic substrate 12.

The upper sensing electrode 318 is made of Pt or Pt/Rh and active against NOx. The upper sensing electrode 318 decomposes NOx into nitrogen ions and oxygen ions. The lower sensing electrode 319 is made of Pt.

The sensing electrodes 418 and 419 of the second sensor cell 41 are connected to the second detecting circuit 42 via leads (not shown) and terminals (not shown) formed on the surfaces of the second solid electrolytic substrate 12.

The upper sensing electrode 418 is made of Pt with an Au additive and inactive against NOx. The lower sensing electrode 419 is made of Pt.

The heater element 190 is patterned along the surface of the heater substrate 191 in an area covering all of the pump cell 21, the first sensor cell 31 and the second sensor cell 41 when seen in an up-and-down direction. The heater element 190 is connected to a power source (not shown) via leads (not shown) and terminals (not shown) formed on the surface of the heater substrate 191. The heater substrate 191 and the coating plate 192 are made of alumina.

A manufacturing method of the above-described composite gas sensor 1 will be explained hereinafter.

First, a manufacturing method of a zirconic green sheet is explained. The zirconic green sheet is used to form the first and second solid electrolytic substrates 11~12 and the substrates 131~133. A main material of the zirconia green sheet is a yttria partially-stabilized zirconia with an average particle diameter of 0.5 $\mu$m. This yttria partially-stabilized zirconia comprises 6 mol % yttria and 94 mol % zirconia. The weighing capacity of the yttria partially-stabilized zirconia is 100 weight parts. As subsidiary materials, an $\alpha$-alumina is one weight part, a PVB (polyvinyl butyral) is five weight parts, a DBP (di-butyl phthalate) is 10 weight parts, an ethanol is 10 weight parts, and a toluene is 10 weight parts.

Then, the prepared yttria partially-stabilized zirconia, the $\alpha$-alumina, the PVB, the DBP, the ethanol and the toluene are mixed in a ball mill to obtain a slurry of them. The obtained slurry is configured into a plane sheet body by using a doctor blade method. The fabricated sheet body is 0.3 mm thick in a dried condition. A rectangular piece of 5 mm×70 mm is cut out of this sheet for each of the above five substrates (i.e., first and second solid electrolytic substrates 11~12 and substrates 131~133).

Next, to form the pumping electrode 218 and the associated leads and terminals, an electrically conductive Pt paste is printed on the upper surface of the fabricated rectangular sheet body of the first solid electrolytic substrate 11. Furthermore, to form the pumping electrode 219 and the associated leads and terminals, an electrically conductive Pt paste with an additive of 1~10 wt % Au is printed on the lower surface of the fabricated rectangular sheet body of the first solid electrolytic substrate 11.

The substrates 133 and 131 are provided with rectangular apertures corresponding to the first and second chambers 101 and 102 of 2 mm×15 mm, respectively. The substrate 132 is provided with the pinhole serving as the diffusive passage 104.

To form the sensing electrode 318 and the associated leads and terminals, an electrically conductive Pt paste with an additive of 0~10 wt % Rh is printed on the upper surface of the fabricated rectangular sheet body of the second solid electrolytic substrate 12. To form the sensing electrode 319 and the associated leads and terminals, an electrically conductive Pt paste is printed on the lower surface of the fabricated rectangular sheet body of the second solid electrolytic substrate 12.

To form the sensing electrode 418 and the associated leads and terminals, an electrically conductive Pt paste with an additive of 1~10 wt % Au is printed on the upper surface of the fabricated rectangular sheet body of the second solid electrolytic substrate 12. To form the sensing electrode 419 and the associated leads and terminals, an electrically conductive Pt paste is printed on the lower surface of the fabricated rectangular sheet body of the second solid electrolytic substrate 12.

Next, a manufacturing method of an alumina green sheet is explained. The alumina green sheet is used to form the substrate 141, the heater substrate 191 and the coating plate 192. A main material of the aluminum green sheet is an $\alpha$-alumina with an average particle diameter of 0.3 $\mu$m. The weighing capacity of this $\alpha$-alumina is 98 weight parts. As subsidiary materials, the yttria partially-stabilized zirconia, comprising 6 mol % yttria and 94 mol % zirconia, is three weight parts. Furthermore, the PVB is 10 weight parts, the DBP is 10 weight parts, the ethanol is 30 weight parts, and the toluene is 30 weight parts.

Then, the prepared $\alpha$-alumina, yttria partially-stabilized zirconia, the PVB, the DBP, the ethanol and the toluene are mixed in a ball mill to obtain a slurry of them. The obtained slurry is configured into a plane sheet body by using the doctor blade method. The fabricated sheet body is 0.3 mm thick in a dried condition. A rectangular piece of 5 mm×70 mm is cut out of this sheet body for each of the substrate 141, the heater substrate 191 and the coating plate 192.

The fabricated rectangular sheet body of the substrate 141 is provided with a slit of 2 mm×65 mm corresponding to the reference gas chamber 103.

To form the heater element 190 and the associated leads and terminals, an electrically conductive Pt paste with an additive of 10 wt % alumina is printed on the upper surface of the fabricated rectangular sheet body of the heater substrate 191.

Next, the rectangular sheet bodies thus fabricated individually are stacked or accumulated in the predetermined order and then pressed at 80° C. to form the multilayered assembly as shown in FIG. 1. The multilayered assembly is then sintered in an atmospheric environment of 1,500° C.

The obtained multilayered sintered body is connected with the pump circuit 22, the first detecting circuit 32 and the second detecting circuit 42, thereby obtaining the composite gas sensor 1.

The composite gas sensor 1 is used in the following manner to measure the gas concentration.

A sample gas is introduced into the first chamber 101 via the pinhole 110. The introduced sample gas diffuses into the second chamber 102 via the diffusive passage 104.

The second sensor cell 41 monitors the oxygen concentration in the second chamber 102. The second sensor cell 41 acts as an oxygen concentration cell capable of generating an electromotive force in response to the oxygen concentration in the second chamber 102. The first voltmeter 421 detects the generated electromotive force of the second sensor cell 41.

The oxygen concentration in the second chamber 102 is adjusted to a predetermined reference concentration by the feedback circuit 25. More specifically, the controller 251 comprises a comparator combined with an operational amplifier. The variable electric power source 229 of the pump circuit 22 is controlled in accordance with an output of the comparator.

When the oxygen concentration in the second chamber 102 is larger than the reference concentration, the first voltmeter 421 produces an output value lower than 0.4 V representing the reference concentration. The output signal of the first voltmeter 421 is entered into the controller 251 to increase the voltage of the variable electric power source 229. In response to an increased voltage, the pump cell 21 promotes the exhaust of the oxygen gas.

When the oxygen concentration in the second chamber 102 is lower than the reference concentration, the first voltmeter 421 produces an output value higher than 0.4 V (i.e., target value). In response to the output signal of the first voltmeter 421, the controller 251 decreases the voltage of the variable electric power source 229. The pump cell 21 suppresses the exhaust of the oxygen gas or introduces the oxygen gas.

Through the above-described control, the oxygen concentration in the first chamber 101 converges to the reference concentration value. The adjusted sample gas flows into the second chamber 102. The oxygen concentration in the second chamber 102 becomes the reference concentration value.

According to the Nernst's equation, the reference concentration value corresponding to 0.4 V of the first voltmeter is 1 ppm or less in terms of the $O_2$ concentration.

The first sensor cell 31 deoxidizes the NOx into oxygen ions when the NOx in the second chamber 102 is brought into contact with the sensing electrode 318. Similarly, the oxygen residing in the second chamber 102 is deoxidized into oxygen ions.

In the first detecting circuit 32, the electric power voltage 329 always applies a constant voltage (i.e., 0.45V) between the sensing electrodes 318 and 319. Thus, the first ammeter 321 measures a limit current responsive to the oxygen ion concentration.

When the oxygen concentration is constant in the second chamber 102, the oxygen ions derived from the residual oxygen is constant. An influence given to the ammeter 321 is constant. Accordingly, the variation of NOx concentration can be known from the measured limit current.

The NOx concentration detector 3 receives the output of the first ammeter 321 to detect the NOx concentration.

As the pump cell voltage is variably controlled to maintain a constant oxygen concentration in the second chamber 102, the pump current is proportional to the air-fuel ratio of the sample gas, i.e., the oxygen amount. The second ammeter 221, connected to the pump cell 21, measures the air-fuel ratio of the sample gas in the second chamber 102.

As described in the forgoing description, the composite gas sensor 1 measures the NOx concentration as well as the air-fuel ratio. This means that the composite gas sensor 1 of the first embodiment operates as a multipurpose gas sensor that detects the deterioration of a catalytic converter in the exhaust gas passage and electronically controls the air-fuel ratio of the gas mixture introduced into the engine combustion chamber.

FIG. 2 is a modified arrangement of the first embodiment shown in FIG. 1. According to the modified arrangement of FIG. 2, the upper pumping electrode 218 of the pump cell 21 is fully covered by an electrode protecting layer 182. A trap layer 181 is mounted on the electrode protecting layer 182. The trap layer 181 traps the poison substances involved in the sample gas. With this arrangement, the upper pumping electrode 218 of the pump cell 21 is surely protected from the poison substances.

FIG. 3 is another modified arrangement of the first embodiment shown in FIG. 1. According to the modified arrangement of FIG. 3, a porous layer 15 is provided at the side wall of the composite gas sensor 1 instead of opening the pinhole 110. The porous layer 15 introduces the sample gas into the first chamber 101 of the sample gas chamber 100. The porous layer 15 is functionally identical with the pinhole 110.

Second Embodiment

Figure 4:
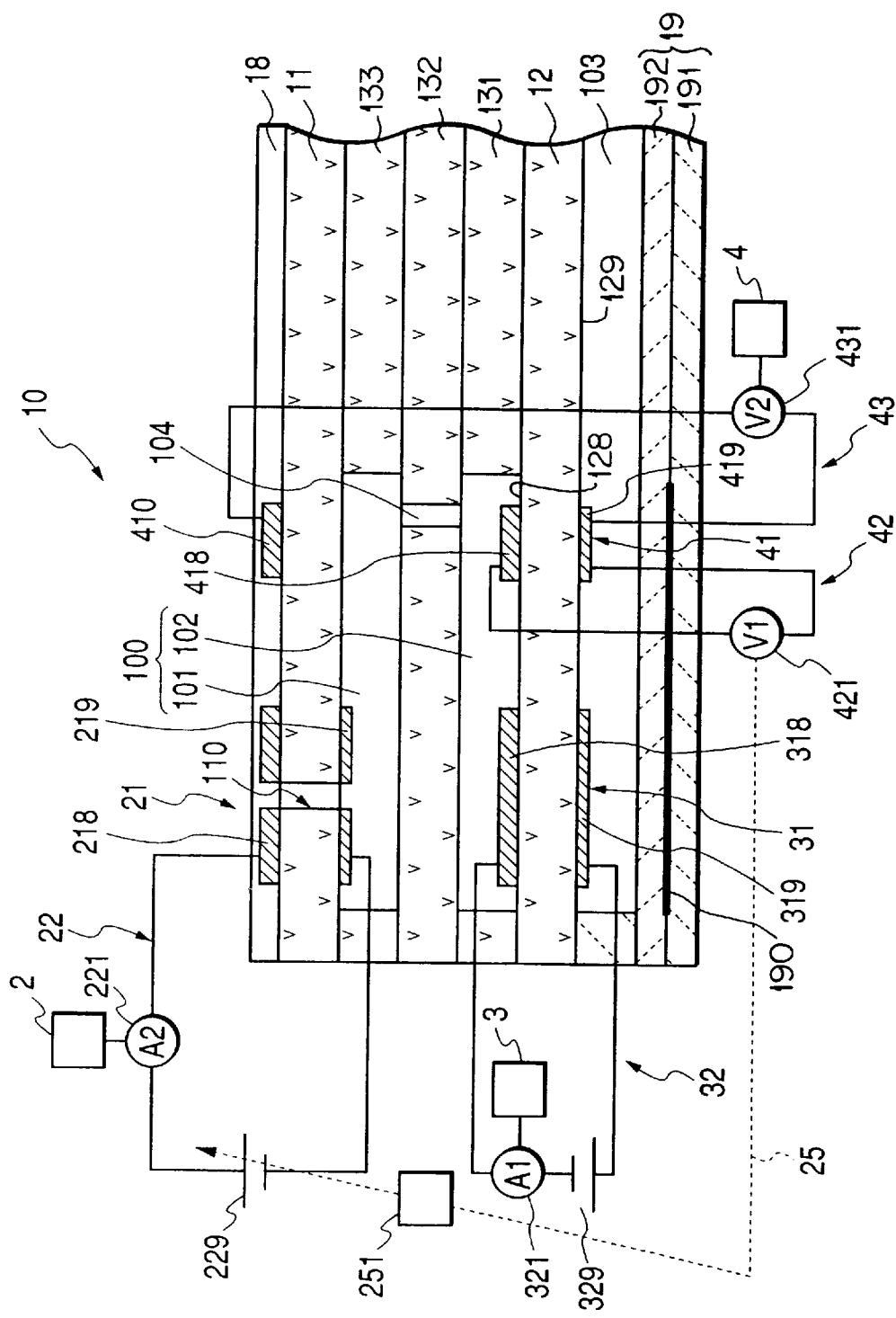
FIG. 4 is a cross-sectional view showing an arrangement of a composite gas sensor in accordance with a second embodiment of the present invention.
Figure 5:
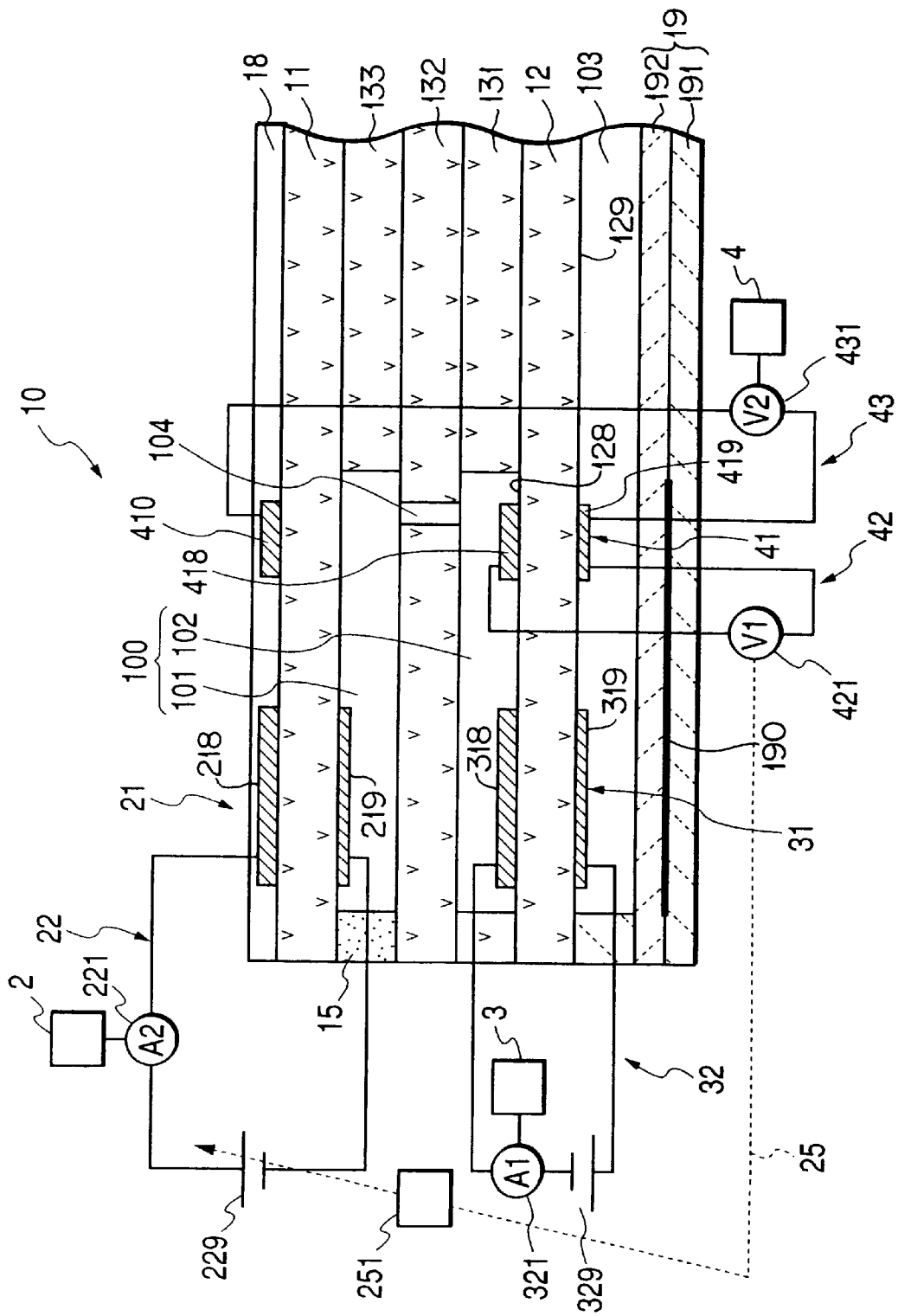
FIG. 5 is a cross-sectional view showing a modified arrangement of the composite gas sensor in accordance with the second embodiment of the present invention.

FIGS. 4 and 5 are cross-sectional views showing preferable arrangements of a composite gas sensor in accordance with a second embodiment of the present invention.

As shown in FIG. 4, a composite gas sensor 10 of the second embodiment comprises a sample gas chamber 100 and a reference gas chamber 103. At least part of the sample gas chamber 100 and the reference gas chamber 103 is defined by first and second solid electrolytic substrates 11 and 12, respectively. The first and second solid electrolytic substrates 11 and 12 are made of an oxygen ion conductive material. A pinhole 110 extends across the first solid electrolytic substrate 11 from an upper surface to a lower surface thereof. A lower end of the pinhole 110 communicates with the sample gas chamber 100. A sample gas is introduced from the outside to the sample gas chamber 100 via the pinhole 110.

The sample gas chamber 100 consists of a first chamber 101 and a second chamber 102 communicating each other via a diffusive passage 104. A protecting layer 18 fully covers a pumping electrode 218 and a later-described external electrode 410 formed on the upper surface of the first solid electrolytic substrate 11.

The composite gas sensor 10 comprises a pump cell 21, a first sensor cell 31 and a second sensor cell 41. The pump cell 21 comprises a pair of pumping electrodes 218 and 219 formed on the upper and lower surfaces of the first solid electrolytic substrate 11, respectively. The first sensor cell 31 comprises a pair of sensing electrodes 318 and 319 formed on the upper and lower surfaces of the second solid electrolytic substrate 12, respectively.

The second embodiment is characterized in that the second sensor cell 41 is associated with a third detecting circuit 43 as well as the second detecting circuit 42.

The second sensor cell 41 comprises a pair of sensing electrodes 418 and 419 formed on the upper and lower surfaces of the second solid electrolytic substrate 12, respectively. The upper sensing electrodes 418 is positioned on the bottom of the second chamber 102 and the lower sensing electrode 419 is positioned on the ceiling of the reference gas chamber 103.

The second sensor cell 41 further comprises the external electrode 410 provided on the upper (i.e., outer) surface of the first solid electrolytic substrate 11. The sensing electrodes 418 and 419 are serially connected with a first voltmeter 421, thereby constituting the second detecting circuit 42. The sensing electrode 419 and the external electrode 410 are serially connected with a second voltmeter 431, thereby constituting the third detecting circuit 43. An oxygen concentration detector 4 is connected to the second voltmeter 431 to measure the oxygen concentration in the sample gas residing in the second chamber 102.

The rest of the arrangement is the same as those disclosed in the first embodiment shown in FIG. 1.

The composite gas sensor 10 is a multipurpose gas sensor capable of detecting the NOx concentration and the air-fuel ratio in the same manner as the above-described composite gas sensor 1 of the first embodiment.

The sensing electrode 419 and the external electrode 410 cooperatively function as an oxygen concentration cell that generates an electromotive force in response to the oxygen concentration in the sample gas flowing outside the composite gas sensor 10. The second voltmeter 431 produces an output representing the generated electromotive force. The oxygen concentration detector 4 detects the oxygen concentration in the sample gas flowing outside the composite gas sensor 10 based on the output signal of the second voltmeter 431.

The composite gas sensor 10 further measures the NOx concentration by the first ammeter 321 and measures the air-fuel ratio by the second ammeter 221.

Accordingly, the composite gas sensor 10 of the second embodiment operates as a multipurpose gas sensor that detects the deterioration of a catalytic converter in the exhaust gas passage, electronically controls the air-fuel ratio of the gas mixture introduced into the engine combustion chamber, and detects the oxygen concentration in the exhaust gas passage.

FIG. 5 is a modified arrangement of the second embodiment shown in FIG. 4. According to the modified arrangement of FIG. 5, a porous layer 15 is provided at the side wall of the composite gas sensor 10 instead of opening the pinhole 110. The porous layer 15 introduces the sample gas into the first chamber 101 of the sample gas chamber 100. The porous layer 15 is functionally identical with the pinhole 110.

Third Embodiment

Figure 6:
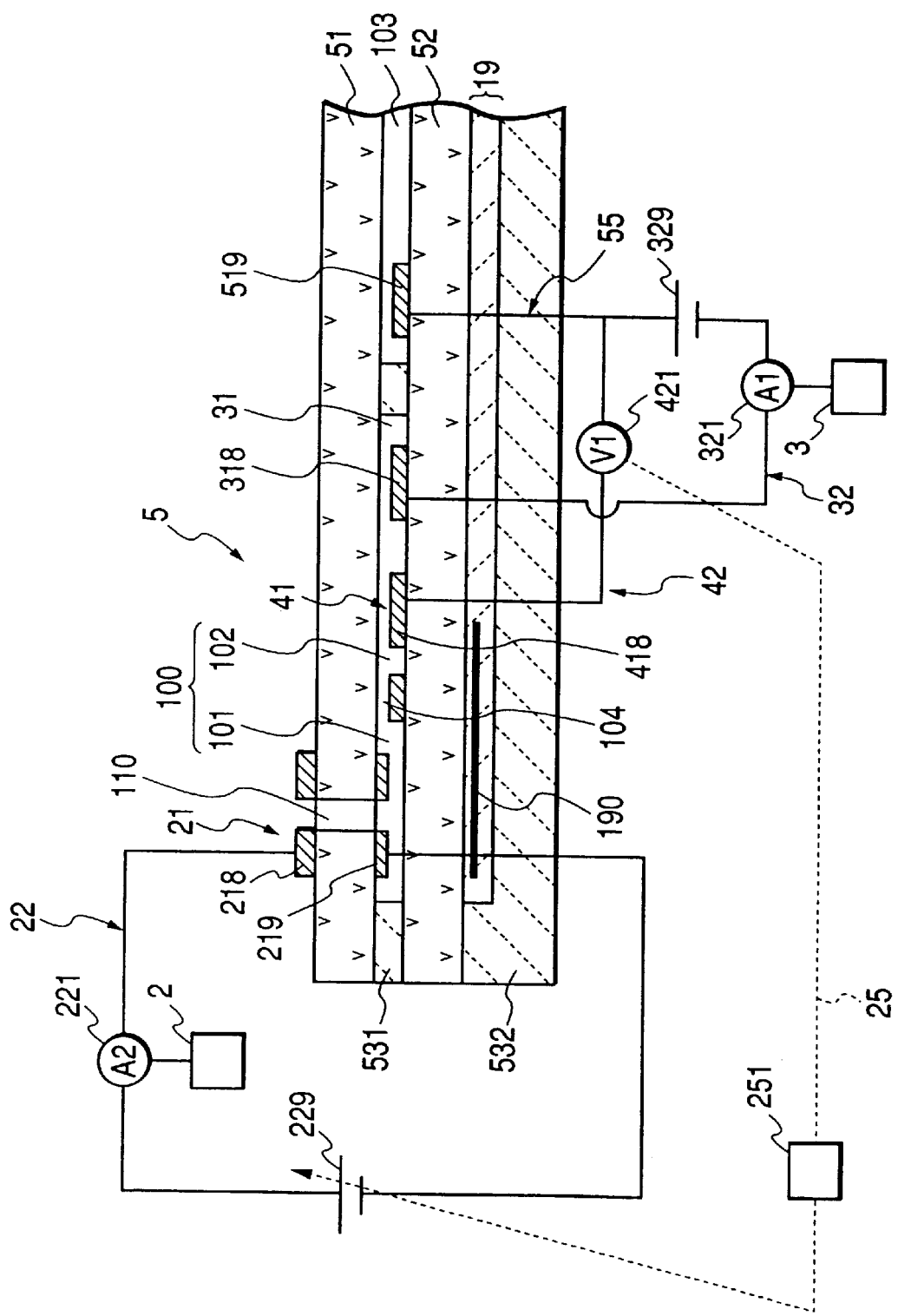
FIG. 6 is a cross-sectional view showing an arrangement of a composite gas sensor in accordance with a third embodiment of the present invention.
Figure 7:
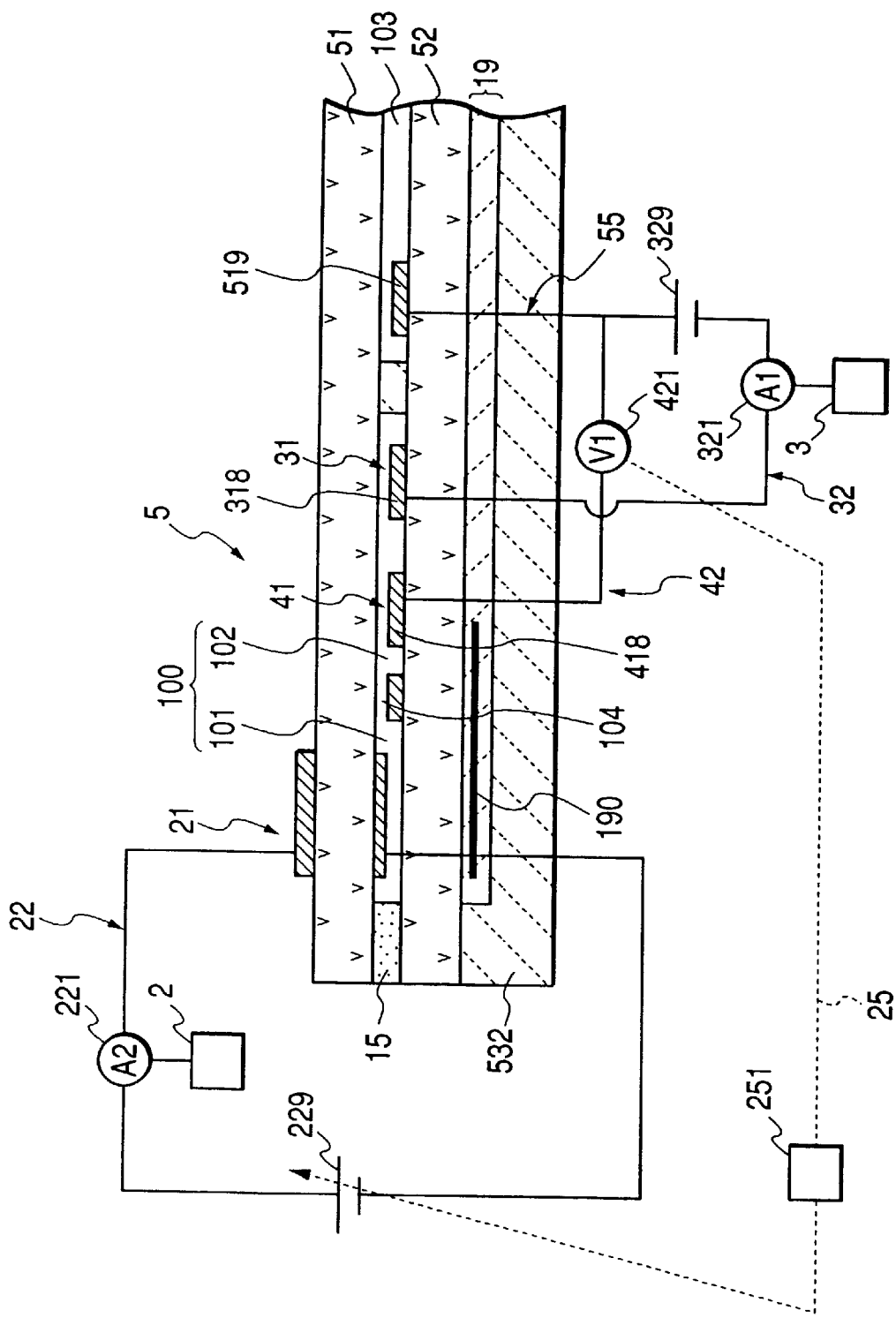
FIG. 7 is a cross-sectional view showing a modified arrangement of the composite gas sensor in accordance with the third embodiment of the present invention.
Figure 8:
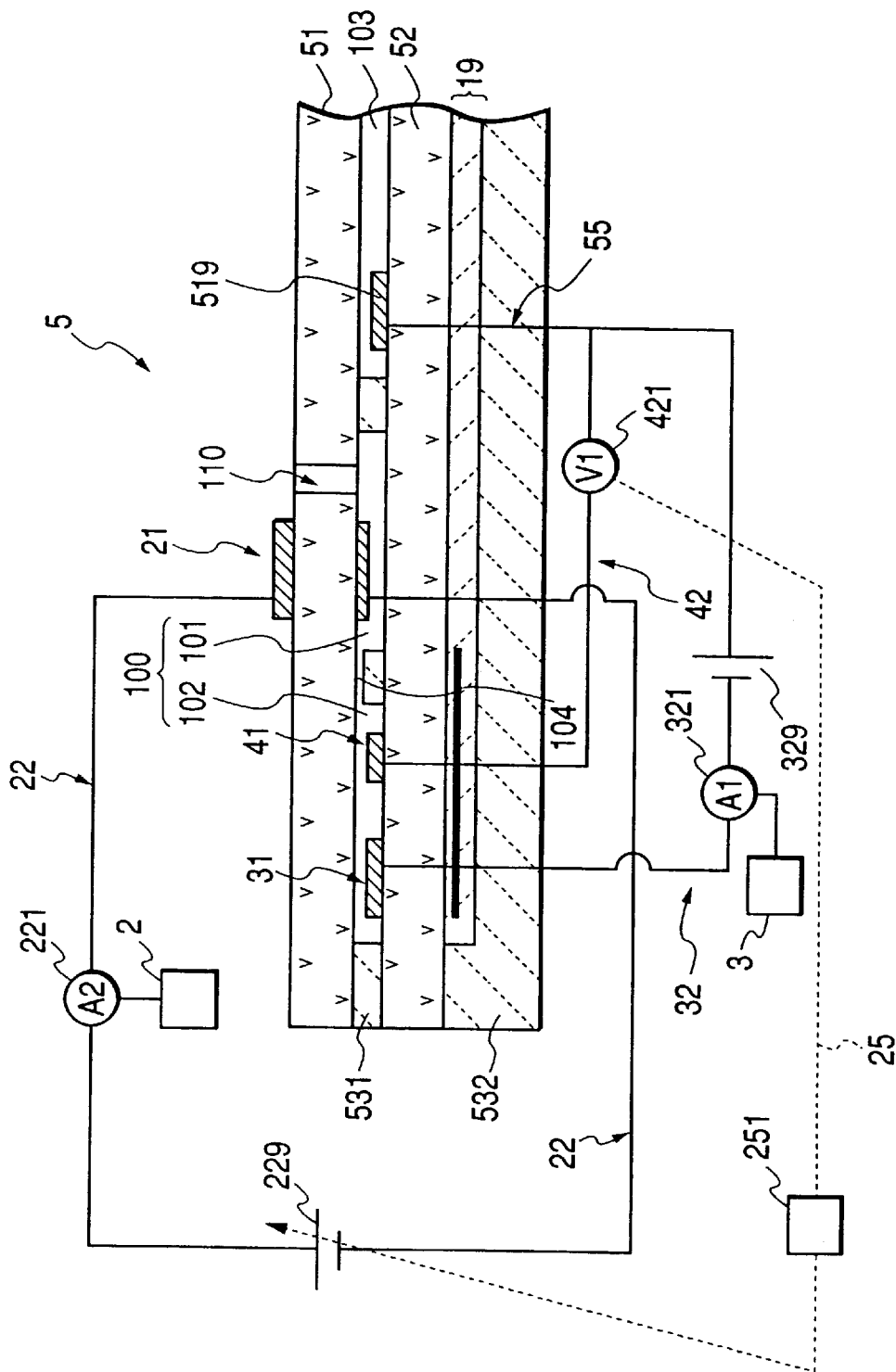
FIG. 8 is a cross-sectional view showing another modified arrangement of the composite gas sensor in accordance with the third embodiment of the present invention.

FIGS. 6 to 8 are cross-sectional views showing preferable arrangements of a composite gas sensor in accordance with a third embodiment of the present invention. The composite gas sensor of the third embodiment is characterized in that the sample gas chamber and the reference gas chamber position at the same surface level.

As shown in FIG. 6, a composite gas sensor 5 of the third embodiment comprises a sample gas chamber 100 and a reference gas chamber 103 defined by first and second solid electrolytic substrates 51 and 52. A pinhole 110 extends across the first solid electrolytic substrate 51 from an upper surface to a lower surface thereof. A lower end of the pinhole 110 communicates with the sample gas chamber 100. A sample gas is introduced from the outside to the sample gas chamber 100 via the pinhole 110. The sample gas chamber 100 consists of a first chamber 101 and a second chamber 102 communicating each other via a diffusive passage 104.

The composite gas sensor 5 comprises a pump cell 21, a first sensor cell 31 and a second sensor cell 41. The pump cell 21 comprises a pair of pumping electrodes 218 and 219 formed on the upper and lower surfaces of the first solid electrolytic substrate 51, respectively. The first sensor cell 31 comprises a pair of sensing electrodes 318 and 519 formed on the same upper surface of the second solid electrolytic substrate 52. The second sensor cell 41 comprises a pair of sensing electrodes 418 and 519 formed on the same upper surface of the second solid electrolytic substrate 52. The sensing electrodes 318 and 418 extend along the bottom of the second chamber 102 of the sample gas chamber 100. The sensing electrode 519 is a common electrode extending along the bottom of the reference gas chamber 103.

That is, according to the arrangement of the third embodiment, the sensing electrodes 318, 418 and 519 of the first and second sensor cells 31 and 41 are positioned at the same surface level (i.e., the upper surface of the second solid electrolytic substrate 52).

The pump cell 21 is connected to the pump circuit 22. The first sensor cell 31 is connected to the first detecting circuit 32. The second sensor cell 41 is connected to the second detecting circuit 42. The first detecting circuit 32 and the second detecting circuit 42 has a common circuit 55 that is connected to the common electrode 519.

An insulating substrate 531 is interposed between the first and second solid electrolytic substrates 51 and 52. The insulating substrate 531 has an aperture defining the sample gas chamber 100 and another aperture defining the reference gas chamber 103. An insulating substrate 532 is located below the second solid electrolytic substrate 52. A plane heater 19 is disposed in a recess provided on the upper surface of the insulating substrate 532.

The rest of the arrangement is the same as those disclosed in the first embodiment. The composite gas sensor of the third embodiment operates in the same manner as the composite gas sensor of the first embodiment in the measurement of the NOx concentration and the detection of the air-fuel ratio.

According to the arrangement of the third embodiment, an overall thickness of the composite gas sensor 5 can be reduced. The flat arrangement of the sample gas chamber 100 and the reference gas chamber 103 positioned at the same level is advantageous in that the heater 19 can be disposed closely to the pump cell 21, the first sensor cell 31 and the second sensor cell 41. This improves the warmup ability of the composite gas sensor 5.

Furthermore, the arrangement of the third embodiment is simple and compact. The electrode 519 provided in the reference gas chamber 103 is commonly used as the common electrode for the first sensor cell 31 and the second sensor cell 41. The first detecting circuit 32 and the second detecting circuit 42 have the common circuit 55 connected to this common electrode 519. This reduces the total amount or length of the leads required for taking out the sensor signals. Furthermore, the manufacturing process can be simplified.

FIG. 7 is a modified arrangement of the third embodiment shown in FIG. 6. According to the modified arrangement of FIG. 7, a porous layer 15 is provided at the side wall of the composite gas sensor 5 instead of opening the pinhole 110. The porous layer 15 introduces the sample gas into the first chamber 101 of the sample gas chamber 100. The porous layer 15 is functionally identical with the pinhole 110.

FIG. 8 is another modified arrangement of the third embodiment shown in FIG. 6. According to the modified arrangement of FIG. 8, the pinhole 110 is provided at a different position offset from the pump cell 21.

Fourth Embodiment

Figure 9:
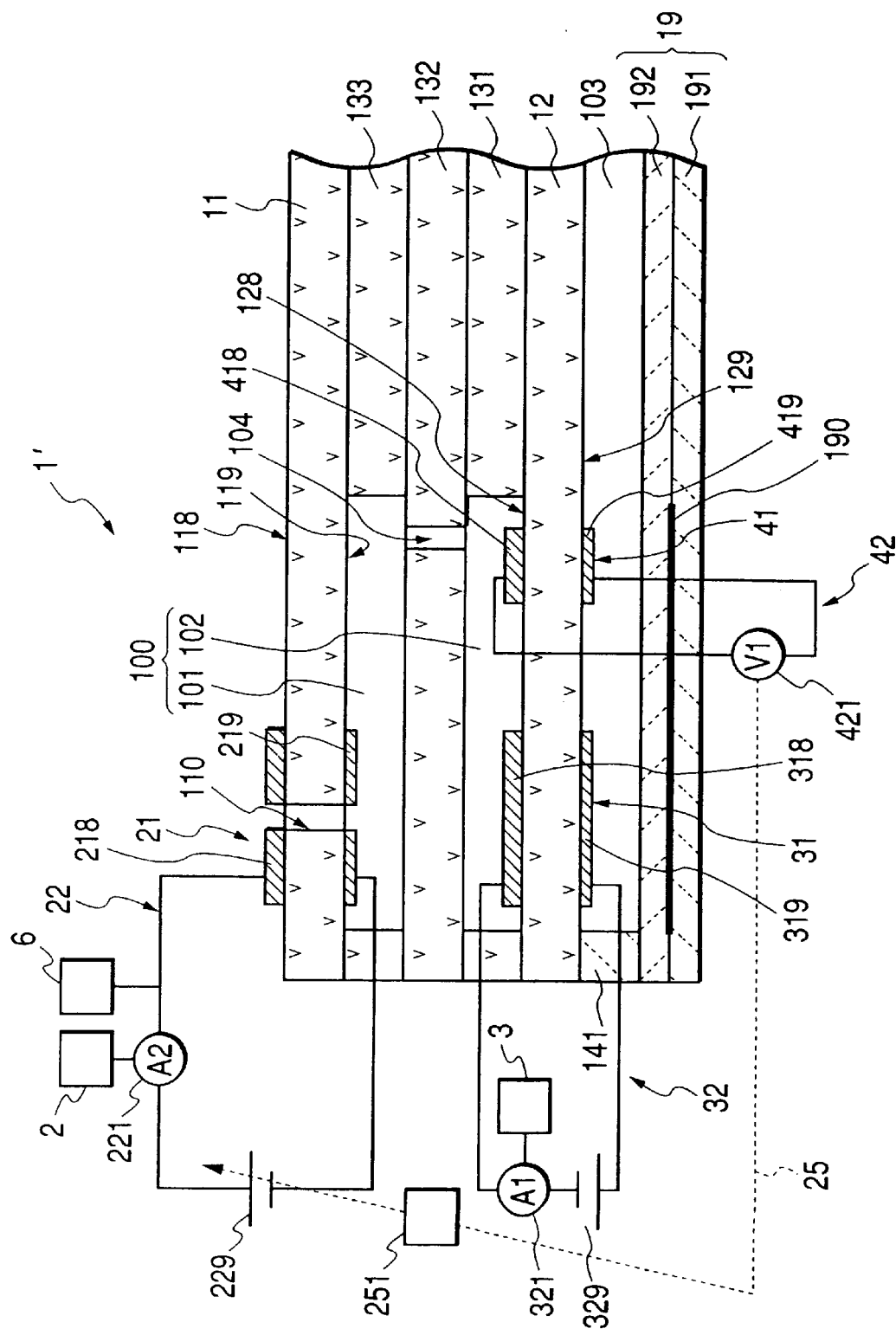
FIG. 9 is a cross-sectional view showing an arrangement of a composite gas sensor in accordance with a fourth embodiment of the present invention.

FIG. 9 is a cross-sectional view showing a preferable arrangement of a composite gas sensor in accordance with a fourth embodiment of the present invention. A composite gas sensor 1 of the fourth embodiment differs from the composite gas sensor 1 of the first embodiment shown in FIG. 1 in that an impedance detector 6 is additionally provided in the pump circuit 22.

The fourth embodiment provides an arrangement for detecting the temperature of the sample gas. The impedance detector 6 measures the impedance of the pump cell 21. In general, the impedance is proportional to the temperature. The pump cell 21 has the function of introducing and exhausting the sample gas into and from the first chamber 101 of the sample gas chamber 100. The temperature of the pump cell 21 is substantially the same as the temperature of the sample gas.

Accordingly, the sample gas temperature can be detected by measuring the impedance of the pump cell 12.

In short, the fourth embodiment provides a multipurpose composite gas sensor capable of detecting the NOx concentration, the air-fuel ratio and the sample gas temperature.

When the composite gas sensor 1' is installed in the exhaust gas passage of an internal combustion, the composite gas sensor 1' detects an undesirable reduction of the exhaust gas temperature. When the engine misfires, the exhaust gas temperature decreases. To prevent such a malfunction, the fourth embodiment makes it possible to carefully feedback control the engine combustion based on the output signal of the composite gas sensor 1'.

Furthermore, the fourth embodiment makes it possible to monitor an abnormal heat generation in the catalytic converter and detect its deterioration.

Fifth Embodiment

Figure 10:
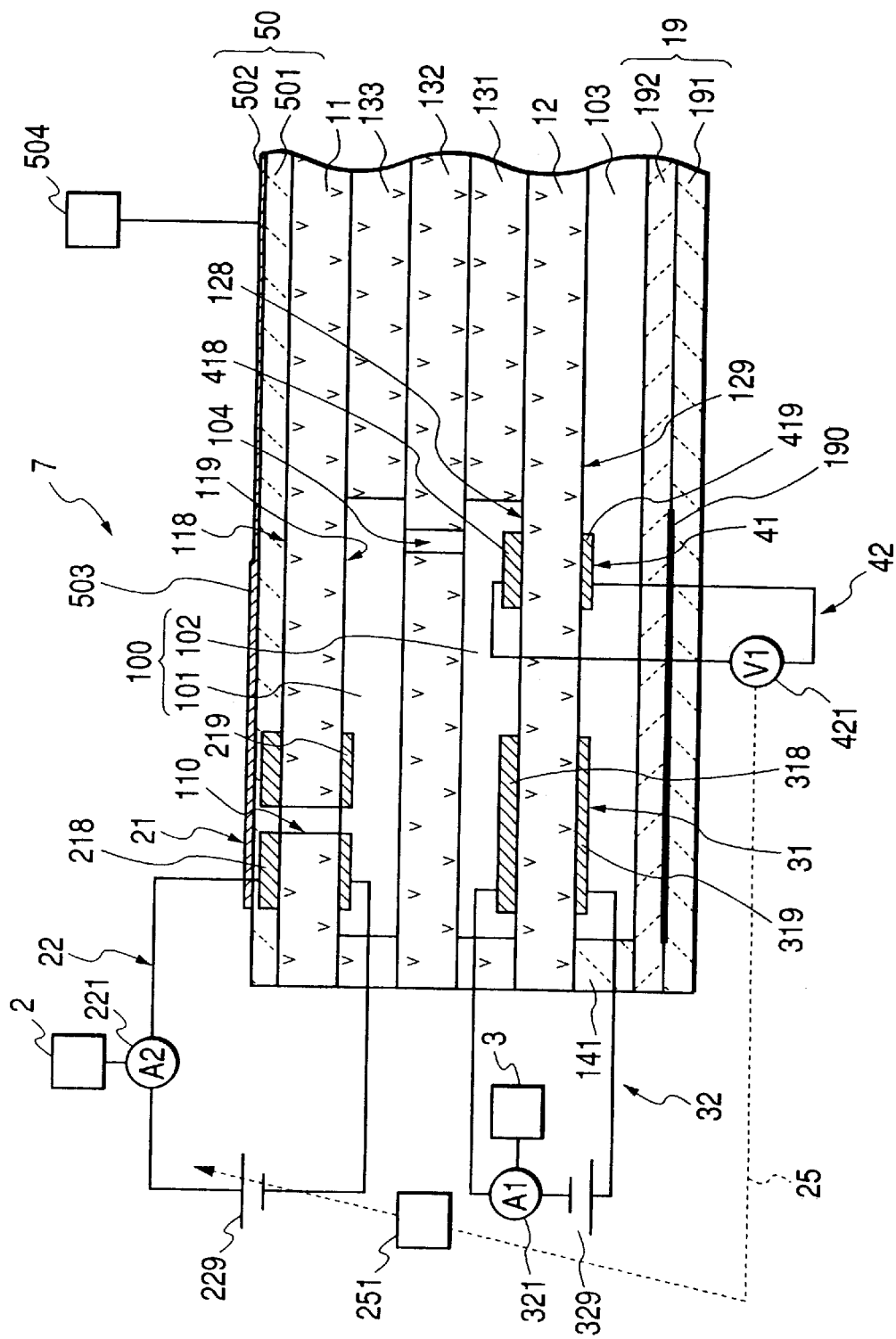
FIG. 10 is a cross-sectional view showing an arrangement of a composite gas sensor in accordance with a fifth embodiment of the present invention.

FIG. 10 is a cross-sectional view showing a preferable arrangement of a composite gas sensor in accordance with a fifth embodiment of the present invention.

As shown in FIG. 10, a composite gas sensor 7 of the fifth embodiment comprises a sample gas chamber 100 and a reference gas chamber 103. At least part of the sample gas chamber 100 and the reference gas chamber 103 is defined by first and second solid electrolytic substrates 11 and 12, respectively. The first and second solid electrolytic substrates 11 and 12 are made of an oxygen ion conductive material. A pinhole 110 extends across the first solid electrolytic substrate 11 from an upper surface to a lower surface thereof. A lower end of the pinhole 110 communicates with the sample gas chamber 100. A sample gas is introduced from the outside to the sample gas chamber 100 via the pinhole 110.

A pump cell 21 comprises a pair of pumping electrodes 218 and 219 formed on an upper surface 118 and a lower surface 119 of the first solid electrolytic substrate 11, respectively. The above-described pinhole 110 has an upper end opened at a center of the upper pumping electrode 218 and a lower end opened at a center of the lower pumping electrode 219. The upper pumping electrode 218 is exposed to the outside. The lower surface 119 of the first solid electrolytic substrate 11 defines a ceiling of the sample gas chamber 100. The lower pumping electrode 219 extends along the ceiling of the sample gas chamber 100. The pump cell 21 adjusts an amount of the oxygen gas introduced or exhausted into or from the sample gas chamber 100.

A temperature detecting cell 50 is integrally mounted on the pump cell 21. The temperature detecting cell 50 is connected to a resistance detector 504. The temperature detecting cell 50 comprises a porous substrate 501. The sample gas pass through this porous substrate 501. A resistor 503 and a lead 502 are provided on an upper surface (i.e., outside) of the porous substrate 501.

A first sensor cell 31 comprises a pair of sensing electrodes 318 and 319 formed on an upper surface 128 and a lower surface 129 of the second solid electrolytic substrate 12, respectively. The upper surface 128 of the second solid electrolytic substrate 12 defines a bottom of the sample gas chamber 100. The upper sensing electrode 318 extends along the bottom of the sample gas chamber 100. The lower surface 129 of the second solid electrolytic substrate 12 defines a ceiling of the reference gas chamber 103. The lower sensing electrode 319 extends along the ceiling of the reference gas chamber 103. The first sensor cell 31 detects the concentration of the NOx gas residing in the sample gas chamber 100.

A second sensor cell 41 comprising a pair of sensing electrodes 418 and 419 formed on the upper surface 128 and the lower surface 129 of the second solid electrolytic substrate 12, respectively. The upper sensing electrode 418 extends along the bottom of the sample gas chamber 100. The lower sensing electrode 419 extends along the ceiling of the reference gas chamber 103. The second sensor cell 41 detects the concentration of the oxygen gas residing in the sample gas chamber 100.

The first sensor cell 31 is serially connected with a first ammeter 321 and an electric power source 329, thereby constituting a first detecting circuit 32. The pump cell 21 is serially connected with a second ammeter 221 and a variable electric power source 229, thereby constituting a pump circuit 22. The second sensor cell 41 is serially connected with a first voltmeter 421, thereby constituting a second detecting circuit 42.

A controller 251 feedback controls the variable electric power source 229 in response to an output value of the first voltmeter 421. In other words, the controller 251 and the first voltmeter 421 cooperatively operate as a feedback circuit 25 for controlling the variable electric power source 229. With this feedback control, the output value of the first voltmeter 421 is maintained at a constant value. A NOx concentration detector 3 is connected with the first ammeter 321. The NOx concentration detector 3 measures the concentration of the NOx gas residing in the sample gas chamber 100 based on an output value of the first ammeter 321. An air-fuel ratio detector 2 is connected with the second ammeter 221. The air-fuel ratio detector 2 measures the air-fuel ratio of the sample gas residing in the sample gas chamber 100 based on an output value of the second ammeter 221.

The sample gas chamber 100 consists of a first chamber 101 and a second chamber 102 partitioned by an intervening substrate 132. A diffusive passage 104 extends across the intervening substrate 132 from the first chamber 101 to the second chamber 102. Thus, the first chamber 101 communicates with the second chamber 102 via the diffusive passage 104.

The above-described pinhole 110 and the lower pumping electrode 219 of the pump cell 21 face the first chamber 101. The upper sensing electrode 318 of the first sensor cell 31 and the upper sensing electrode 418 of the second sensor cell 41 face the second chamber 102.

The first solid electrolytic substrate 11 defines a ceiling of the first chamber 101. The substrate 132 defines a bottom of the first chamber 101. A substrate 133, interposed between the first solid electrolytic substrate 11 and the substrate 132, has an aperture defining the side walls of the first chamber 101.

The substrate 132 defines a ceiling of the second chamber 102. The second solid electrolytic substrate 12 defines a bottom of the second chamber 102. A substrate 131, interposed between the substrate 132 and the second solid electrolytic substrate 12, has an aperture defining the side walls of the second chamber 102.

A bottom of the reference gas chamber 103 is defined by an upper surface of a heater 19 integrally provided at the lower end of the composite gas sensor 7. A substrate 141, interposed between the second solid electrolytic substrate 12 and the heater 19, has an aperture (slit) defining the side walls of the reference gas chamber 103.

The heater 19 comprises a heater substrate 191. A heater element 190 is mounted on this heater substrate 191 as a heat generating source. The heater element 190 is covered by a coating plate 192.

As described above, the controller 251 feedback controls the variable electric power source 229 to produce a constant output from the first voltmeter 421.

With this arrangement, the composite gas sensor 7 measures the NOx concentration of the sample gas based on the output value of the first ammeter 321 and measures the air-fuel ratio of the sample gas based on the output value of the second ammeter 221.

Furthermore, the resistance detector 504 of the temperature detecting cell 50 measures the sample gas temperature based on the resistance value of the resistor 503.

As shown in FIG. 10, the composite gas sensor 7 has a multilayered body comprising the porous substrate 501, the first and second solid electrolytic substrates 11~12, the substrates 131~133, 141 and the heater 19. The substrates 131, 132 and 133 are made of the same material as that of the first and second solid electrolytic substrates 11 and 12. The substrate 141 is made of the same material as that of the heater substrate 191 and the coating plate 192. The porous substrate is materially identical with the heater substrate 191 and the coating plate 192 but different in the porosity.

The pumping electrodes 218 and 219 of the pump cell 21 are connected to the pump circuit 22 via leads (not shown) and terminals (not shown) formed on the surfaces of the first solid electrolytic substrate 11.

The lower pumping electrode 219 is made of Pt with an Au additive and inactive against NOx. The upper pumping electrode 218 is made of Pt.

The sensing electrodes 318 and 319 of the first sensor cell 31 are connected to the first detecting circuit 32 via leads (not shown) and terminals (not shown) formed on the surfaces of the second solid electrolytic substrate 12.

The upper sensing electrode 318 is made of Pt or Pt/Rh and active against NOx. The upper sensing electrode 318 decomposes NOx into nitrogen ions and oxygen ions. The lower sensing electrode 319 is made of Pt.

The sensing electrodes 418 and 419 of the second sensor cell 41 are connected to the second detecting circuit 42 via leads (not shown) and terminals (not shown) formed on the surfaces of the second solid electrolytic substrate 12.

The upper sensing electrode 418 is made of Pt with an Au additive and inactive against NOx. The lower sensing electrode 419 is made of Pt.

The heater element 190 is patterned along the surface of the heater substrate 191 in an area covering all of the pump cell 21, the first sensor cell 31 and the second sensor cell 41 when seen in an up-and-down direction. The heater element 190 is connected to a power source (not shown) via leads (not shown) and terminals (not shown) formed on the surface of the heater substrate 191. The heater substrate 191 and the coating plate 192 are made of alumina.

The porous substrate 501 of the temperature detecting cell 50 is an insulating substance made of alumina or the like. The porosity of the porous substrate 501 is in a range of 5~15%. A resistance-temperature coefficient of the resistor 503 is larger than a resistance-temperature coefficient of the lead 502. The resistance value of the resistor 503 is ten times or more the resistance value of the lead 502.

A manufacturing method of the above-described composite gas sensor 7 will be explained hereinafter.

First, a manufacturing method of a zirconic green sheet is explained. The zirconic green sheet is used to form the first and second solid electrolytic substrates 11~12 and the substrates 131~133. A main material of the zirconia green sheet is the yttria partially-stabilized zirconia with an average particle diameter of 0.5 $\mu$m. This yttria partially-stabilized zirconia comprises 6 mol % yttria and 94 mol % zirconia. The weighing capacity of the yttria partially-stabilized zirconia is 100 weight parts. As subsidiary materials, the α-alumina is one weight part, the PVB is five weight parts, the DBP is 10 weight parts, the ethanol is 10 weight parts, and the toluene is 10 weight parts.

Then, the prepared yttria partially-stabilized zirconia, the α-alumina, the PVB, the DBP, the ethanol and the toluene are mixed in a ball mill to obtain a slurry of them. The obtained slurry is configured into a plane sheet body by using the doctor blade method. The fabricated sheet body is 0.3 mm thick in a dried condition. A rectangular piece of 5 mm×70 mm is cut out of this sheet for each of the above five substrates (i.e., first and second solid electrolytic substrates 11~12 and substrates 131~133).

Next, to form the pumping electrode 218 and the associated leads and terminals, an electrically conductive Pt paste is printed on the upper surface of the fabricated rectangular sheet body of the first solid electrolytic substrate 11. Furthermore, to form the pumping electrode 219 and the associated leads and terminals, an electrically conductive Pt paste with an additive of 1~10 wt % Au is printed on the lower surface of the fabricated rectangular sheet body of the first solid electrolytic substrate 11.

The substrates 133 and 131 are provided with rectangular apertures corresponding to the first and second chambers 101 and 102 of 2 mm×15 mm, respectively. The substrate 132 is provided with the pinhole serving as the diffusive passage 104.

To form the sensing electrode 318 and the associated leads and terminals, an electrically conductive Pt paste with an additive of 0~10 wt % Rh is printed on the upper surface of the fabricated rectangular sheet body of the second solid electrolytic substrate 12. To form the sensing electrode 319 and the associated leads and terminals, an electrically conductive Pt paste is printed on the lower surface of the fabricated rectangular sheet body of the second solid electrolytic substrate 12.

To form the sensing electrode 418 and the associated leads and terminals, an electrically conductive Pt paste with an additive of 1~10 wt % Au is printed on the upper surface of the fabricated rectangular sheet body of the second solid electrolytic substrate 12. To form the sensing electrode 419 and the associated leads and terminals, an electrically conductive Pt paste is printed on the lower surface of the fabricated rectangular sheet body of the second solid electrolytic substrate 12.

Next, a manufacturing method of a first alumina green sheet is explained. The first alumina green sheet is used to form the substrate 141, the heater substrate 191 and the coating plate 192. A main material of the aluminum green sheet is the α-alumina with an average particle diameter of 0.3 μm. The weighing capacity of this α-alumina is 98 weight parts. As subsidiary materials, the yttria partially-stabilized zirconia, comprising 6 mol % yttria and 94 mol % zirconia, is three weight parts. Furthermore, the PVB is 10 weight parts, the DBP is 10 weight parts, the ethanol is 30 weight parts, and the toluene is 30 weight parts.

Then, the prepared α-alumina, the yttria partially-stabilized zirconia, the PVB, the DBP, the ethanol and the toluene are mixed in a ball mill to obtain a slurry of them. The obtained slurry is configured into a plane sheet body by using the doctor blade method. The fabricated sheet body is 0.3 mm thick in a dried condition. A rectangular piece of 5 mm×70 mm is cut out of this sheet body for each of the substrate 141, the heater substrate 191 and the coating plate 192.

The fabricated rectangular sheet body of the substrate 141 is provided with a slit of 2 mm×65 mm corresponding to the reference gas chamber 103.

To form the heater element 190 and the associated leads and terminals, an electrically conductive Pt paste with an additive of 10 wt % alumina is printed on the upper surface of the fabricated rectangular sheet body of the heater substrate 191.

Next, a second alumina green sheet used for forming the porous substrate 501 will be explained. A main material of the second aluminum green sheet is an α-alumina with an average particle diameter of 0.4 μm. The weighing capacity of this α-alumina is 100 weight parts. As subsidiary materials, the PVB is 10 weight parts, the DBP is 10 weight parts, the ethanol is 30 weight parts, and the toluene is 30 weight parts.

Then, the prepared α-alumina, the PVB, the DBP, the ethanol and the toluene are mixed in a ball mill to obtain a slurry of them. The obtained slurry is configured into a plane sheet body by using the doctor blade method. The fabricated sheet body is 0.3 mm thick in a dried condition. A rectangular piece of 5 mm×70 mm is cut out of this sheet body for the porous substrate 501.

To form the resistor 503, an electrically conductive Pt paste with an additive of 10 wt % alumina is printed on the upper surface of the fabricated rectangular sheet body of the porous substrate 501. To form the lead 502, an electrically conductive Pt/Rh paste with an additive of 10 wt % alumina is printed on the upper surface of the fabricated rectangular sheet body of the porous substrate 501.

Next, the rectangular sheet bodies thus fabricated individually are stacked or accumulated in the predetermined order and then pressed at 80° C. to form the multilayered assembly as shown in FIG. 10. The multilayered assembly is then sintered in an atmospheric environment of 1,500° C.

The obtained multilayered sintered body is connected with the pump circuit 22, the first detecting circuit 32 and the second detecting circuit 42, thereby obtaining the composite gas sensor 7.

The composite gas sensor 7 is used in the following manner to measure the gas concentration.

A sample gas is introduced into the first chamber 101 via the pinhole 110. The introduced sample gas diffuses into the second chamber 102 via the diffusive passage 104.

The second sensor cell 41 monitors the oxygen concentration in the second chamber 102. The second sensor cell 41 acts as an oxygen concentration cell capable of generating an electromotive force in response to the oxygen concentration in the second chamber 102. The first voltmeter 421 detects the generated electromotive force of the second sensor cell 41.

The oxygen concentration in the second chamber 102 is adjusted to a predetermined reference concentration by the feedback circuit 25. More specifically, the controller 251 comprises a comparator combined with an operational amplifier. The variable electric power source 229 of the pump circuit 22 is controlled in accordance with an output of the comparator.

When the oxygen concentration in the second chamber 102 is larger than the reference concentration, the first voltmeter 421 produces an output value lower than 0.4 V representing the reference concentration. The output signal of the first voltmeter 421 is entered into the controller 251 to increase the voltage of the variable electric power source 229. In response to an increased voltage, the pump cell 21 promotes the exhaust of the oxygen gas.

When the oxygen concentration in the second chamber 102 is lower than the reference concentration, the first voltmeter 421 produces an output value higher than 0.4 V (i.e., target value). In response to the output signal of the first voltmeter 421, the controller 251 decreases the voltage of the variable electric power source 229. The pump cell 21 suppresses the exhaust of the oxygen gas or introduces the oxygen gas.

Through the above-described control, the oxygen concentration in the first chamber 101 converges to the reference concentration value. The adjusted sample gas flows into the second chamber 102. The oxygen concentration in the second chamber 102 becomes the reference concentration value.

According to the Nernst's equation, the reference concentration value corresponding to 0.4 V of the first voltmeter is 1 ppm or less in terms of the $O_2$ concentration.

The first sensor cell 31 deoxidizes the NOx into oxygen ions when the NOx in the second chamber 102 is brought into contact with the sensing electrode 318. Similarly, the oxygen residing in the second chamber 102 is deoxidized into oxygen ions.

In the first detecting circuit 32, the electric power voltage 329 always applies a constant voltage (i.e., 0.45V) between the sensing electrodes 318 and 319. Thus, the first ammeter 321 measures a limit current responsive to the oxygen ion concentration.

When the oxygen concentration is constant in the second chamber 102, the oxygen ions derived from the residual oxygen is constant. An influence given to the ammeter 321 is constant. Accordingly, the variation of NOx concentration can be known from the measured limit current.

The NOx concentration detector 3 receives the output of the first ammeter 321 to detect the NOx concentration.

As the pump cell voltage is variably controlled to maintain a constant oxygen concentration in the second chamber 102, the pump current is proportional to the air-fuel ratio of the sample gas, i.e., the oxygen amount. The second ammeter 221, connected to the pump cell 21, measures the air-fuel ratio of the sample gas in the second chamber 102.

As described in the forgoing description, the composite gas sensor 7 measures the NOx concentration as well as the air-fuel ratio. This means that the composite gas sensor 7 of the fifth embodiment operates as a multipurpose gas sensor that detects the deterioration of a catalytic converter in the exhaust gas passage and electronically controls the air-fuel ratio of the gas mixture introduced into the engine combustion chamber.

Furthermore, according to the fifth embodiment, the resistor 503 of the temperature detecting cell 50 is variable in response to the sample gas temperature. Thus, the sample gas temperature can be measured by detecting the resistance value of the resistor 503 by the resistance detector 504.

In other words, the fifth embodiment provides a multipurpose composite gas sensor capable of detecting the NOx concentration of the sample gas, the air-fuel ratio, and the sample gas temperature.

This invention may be embodied in several forms without departing from the spirit of essential characteristics thereof. The present embodiments as described are therefore intended to be only illustrative and not restrictive, since the scope of the invention is defined by the appended claims rather than by the description preceding them. All changes that fall within the metes and bounds of the claims, or equivalents of such metes and bounds, are therefore intended to be embraced by the claims.

What is claimed is:

1. A composite gas sensor comprising:
   a plurality of solid electrolytic substrates defining at least part of a reference gas chamber and a sample gas chamber;
   a sample gas introducing passage introducing a sample gas into said sample gas chamber;
   a heater member for heating said solid electrolytic substrates;
   a pump cell having a pair of pumping electrodes for discharging oxygen gas contained in the sample gas introduced in said sample gas chamber by a predetermined amount, with one pumping electrode being located on a surface defining said sample gas chamber and the other pumping electrode being exposed to the sample gas not introduced in said sample gas introducing passage;
   a first sensor cell having a pair of oxygen sensing electrodes for generating an electromotive force indicative of an oxygen concentration in said sample gas chamber, with one oxygen sensing electrode being located in said sample gas chamber and the other oxygen sensing electrode being located in said reference gas chamber;
   a second sensor cell having a pair of NOx sensing electrodes for detecting a NOx concentration of the sample gas residing in said sample gas chamber after the pumping operation performed by said pumping cell, with one NOx sensing electrode being located in said sample gas chamber and the other NOx sensing electrode being located in said reference gas chamber;
   a third sensor cell having a pair of oxygen concentration sensing electrodes for generating an electromotive force indicative of an oxygen concentration of the sample gas residing in said sample gas chamber prior to said pumping operation performed by said pumping cell, with one oxygen concentration sensing electrode being located in said reference gas chamber and the other oxygen concentration sensing electrode being exposed to said sample gas not introduced in said sample gas introducing passage;
   said other pumping electrode and said other oxygen concentration sensing electrode being provided on the same surface of an outermost solid electrolytic substrate; and
   said other pumping electrode being disposed closer to a front end of said composite gas sensor than said other oxygen concentration sensing electrode.

2. The composite gas sensor of claim 1, wherein said first sensor cell and said second sensor cell are provided on the same inner solid electrolytic substrate.

3. The composite gas sensor of claim 2, further comprising:
   a pump circuit including a second ammeter and a variable electric power source connected to said pump cell for measuring a current of said pump cell;
   a first detecting circuit including a first ammeter and an electric power source connected to said second sensor cell for measuring a current of said second sensor cell;
   a second detecting circuit including a first voltmeter connected to said first sensor cell for measuring a sensing voltage of said first sensor cell;
   a third detecting circuit including a second voltmeter connected to said third sensor cell for measuring a voltage of said third sensor cell;
   a controller responsive to said sensing voltage of said first sensor cell and adjusting said variable electric power source of said pump circuit to produce a constant value from said first voltmeter;
   a NOx concentration detector associated with said first detecting circuit for determining the NOx concentration of said sample gas based on a measurement by said first ammeter;
   an air-fuel ratio detector associated with said pump circuit for determining an air-fuel ratio of said sample gas based on a measurement by said second ammeter; and
   an oxygen detector associated with said third detecting circuit for determining an oxygen concentration of said sample gas based on a measurement by said second voltmeter.

4. The composite gas sensor of claim 1, wherein said first sensor cell and said third sensor cell share a common reference gas electrode.

5. The composite gas sensor of claim 1, wherein said sample gas introducing passage is a pinhole.

6. The composite gas sensor of claim 1, wherein said solid electrolytic substrates are porous, and wherein said sample gas introducing passage is formed by a porous layer having a porosity larger than that of said solid electrolytic substrates.

* * * * *